US007078531B2

(12) United States Patent
Torrens Jover et al.

(10) Patent No.: US 7,078,531 B2
(45) Date of Patent: Jul. 18, 2006

(54) PROCESS FOR OBTAINING ENANTIOMERS OF THIENYLAZOLYLALCOXYETHANAMINES

(75) Inventors: Antoni Torrens Jover, Barcelona (ES); Helmut H. Buschmann, Barcelona (ES); Stefan Dahmen, Aachen (DE); Matthias Lormann, Aachen (DE)

(73) Assignee: Laboratories Del Dr. Esteve, S.A. (ES)

( * ) Notice: Subject to any disclaimer, the term of this patent is extended or adjusted under 35 U.S.C. 154(b) by 12 days.

(21) Appl. No.: 11/041,638

(22) Filed: Jan. 24, 2005

(65) Prior Publication Data

US 2006/0135787 A1  Jun. 22, 2006

(30) Foreign Application Priority Data

Dec. 17, 2004  (EP)  ................. 04380265

(51) Int. Cl.
*C07D 231/12* (2006.01)
(52) U.S. Cl. ................. 548/365.7
(58) Field of Classification Search ........ 548/365.7
See application file for complete search history.

(56) References Cited

U.S. PATENT DOCUMENTS 6,118,009 A * 9/2000 Torrens-Jover et al. .. 548/375.1

FOREIGN PATENT DOCUMENTS

| EP | 0 289 380 | 12/1994 |
|---|---|---|
| EP | 1 072 266 | 1/2001 |
| WO | WO 99/02500 | 1/1999 |
| WO | WO 99/52525 | 10/1999 |

OTHER PUBLICATIONS

Bolm, Carsten, et al., *Synthesis of Novel 1,1'-Bis(oxazolinyl) metallocenes and their Application in the Asymmertic Phenyl Transfer from Organozincs to Aldehydes*, Journal of Organometallic Chemistry vol. 624, (2001) 157-161.
Bolm, Carsten, et al., *Polymer-Supported Ferrocenyl Oxazolines for the Catalyzed Highly Enantioselective Phenyl Transfer to Aldehydes*, Bioorganic & Medicinal Chemistry Letters vol. 12, (2002) 1795-1798.
Bolm, Carsten, et al., *Catalyzed Asymmetric Aryl Transfer Reactions to Aldehydes with Boronic Acids as Aryl Source*, J. Am. Chem. Soc. vol. 124, (2002) 14850-14851.
Dosa, Peter I., et al., *Planar-Chiral Heterocycles as Ligands in Metal-Catalyzed Processes: Enantioselective Addition of Organozinc Reagents to Aldehydes*, J. Org. Chem. vol. 62, (1997) 444-445.
Fontes, Montserrat, et al., *2-Piperidino-1,1,2-Triphenylethanol: A Highly Effective Catalyst for the Enantioselective Arylation of Aldehydes*, J. Org. Chem. vol. 69, (2004) 2532-2543.
Huang, Wei-Sheng, et al., *New and Improved Ligands for Highly Enantioselective Catalytic Diphenylzinc Additions to Aryl Aldehydes*, Tetrahedron Letters vol. 41, (2000) 145-149.
Noyori, Ryoji, et al., *Asymmetric Catalysis by Architectural and Functional Molecular Engineering: Practical Chemo- and Stereoselective Hydrogenation of Ketones*, Angew. Chem. Int. Ed., vol. 40, (2001) 40-73.
Rudolph, Jens, et al., *High Enantioselective Synthesis of Secondary Alcohols Using Triphenylborane*, Adv. Synth. Catal. vol. 346, (2004) 867-872.
Shibata, Takanori, et al., *Highly Enantioselective Catalytic Asymmetric Automultiplication of Chiral Pyrimidyl Alcohol*, J. Am. Chem. Soc. vol. 118, (1996) 471-472.
Smith, Thomas E., et al., *Effects of Base, Electrophile, and Substrate on the Selective Alkylation of Heteroaromatic Systems*, Heterocycles, vol. 57, (2002) 1211-1217.
Bolm, Carsten et al., *Catalyzed Asymmetric Arylation Reactions*, Angew. Chem. Int. Ed., vol. 40 (2001), 3284-3308.
Pelter, Andrew, et al., *Aryl Coupling Through Borate Complexes with Ethanolamine*, Tetrahedron Letters, vol. 25, No. 4 (1984), 453-456.

* cited by examiner

*Primary Examiner*—Kamal A. Saeed
(74) *Attorney, Agent, or Firm*—Steven J. Hultquist; Intellectual Property/Technology Law

(57) ABSTRACT

A process is described for the preparation of a precursor alcohol of (±)-2-[thienyl(1-methyl-1H-pyrazol-5-yl)methoxy]-N,N-dimethyletanamine and in general for thienylazolylalcoxyethanamines and their enantiomers. The process involves asymmetric addition of a metalated thienyl reagent to a pyrazolcarbaldehyde in the presence of a chiral ligand to yield chiral alcohols. The chiral alcohols are further O-alkylated to yield the corresponding pharmaceutically active thienylazolylalcoxyethanamines.

20 Claims, No Drawings

PROCESS FOR OBTAINING ENANTIOMERS OF THIENYLAZOLYLALCOXYETHANAMINES

CROSS-REFERENCE TO RELATED APPLICATION

The priority of European Patent Application EP04380265.1 filed Dec. 17, 2004 is hereby claimed under the provisions of 35 USC § 119.

FIELD OF THE INVENTION

The present invention relates to a new process for the preparation of enantiomerically enriched carbinols substituted simultaneously with pyrazolyl and thienyl heterocycles. The process comprises the enantioselective addition reaction of a thienyl zinc reagent to a pyrazolcarbaldehyde. The carbinols are useful intermediates for the preparation of pharmaceutically active thyenylazolylalcoxyethanamines.

BACKGROUND OF THE INVENTION

The compound (±)-2-[phenyl(1-methyl-1H-pyrazol-5-yl)methoxy]-N,N-dimethylethanamine, also referred to as (±)-5-[α-(2-dimethylaminoethoxy)benzyl]-1-methyl-1H-pyrazole, or Cizolirtine, of the formula

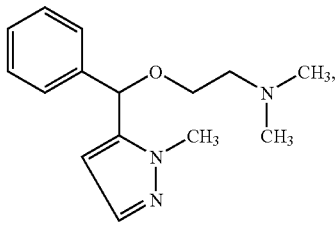

is described in the European Patent EP 289 380. This compound is a potent analgesic which is currently in phase II clinical trials. Optical resolution by fractional crystallization with optically active acids has been applied to the Cizolirtine racemate (International Patent Publication WO 99/02500). The study of their analgesic activities has shown that the dextrorotatory enantiomer, (+)-Cizolirtine, is more potent than the (−)-Cizolirtine.

A further family of active compounds wherein a thiophene ring is present instead of the phenyl ring has been described in International Patent Publication WO 99/52525. Among them, the compound (±)-2-[thienyl(1-methyl-1H-pyrazol-5-yl)methoxy]-N,N-dimethylethanamine, of formula (I)

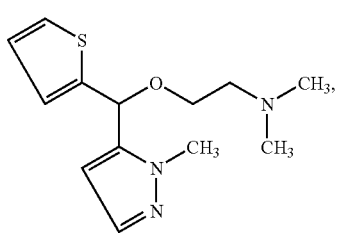

is currently in clinical trials for the treatment of depression. It can be prepared by O-alkylation of the compound of formula II:

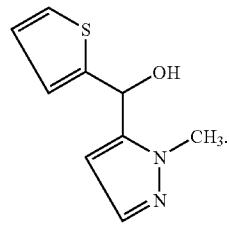

The carbinols such as the one of formula II are key intermediates to reach the compounds described in International Patent Publication WO 99/52525. The pure enantiomers of (+)-I and (−)-I may be prepared by separately O-alkylating the enantiomerically pure intermediates (+)-II and (−)-II. Thus, a synthetic process to the enantiomerically pure/enriched intermediates (+)-II and (−)-II is needed.

The enantioselective reduction of prochiral ketones has been proposed in organic synthesis to obtain secondary alcohols with high enantiomeric purity. Accordingly, a number of strategies for the asymmetric reduction of prochiral ketones to single enantiomer alcohols have been developed [R. Noyori, T. Ohkuma, *Angew. Chem. Int. Ed.*, 2001, 40, 40–73, Wiley-VCH Verlag]. However, no procedure has been described yet for methanols substituted with two heterocycles.

A phenyl transfer reaction to aryl aldehydes as an approach towards enantio-pure diarylalcohols has also been proposed, as alternative to the enantioselective reduction of prochiral ketones [P. I. Dosa, J. C. Ruble, G. C. Fu, *J. Org. Chem.* 1997, 62 444; W. S. Huang, L. Pu, *Tetrahedron Lett.* 2000, 41, 145; M. Fontes, X. Verdaguer, L. Solà, M. A. Pericàs, A. Riera, *J. Org. Chem.* 2004, 69, 2532]. For this transformation, the group of Bolm et al. developed a protocol that utilizes a ferrocene-based ligand (or catalyst) and diphenylzinc in combination with diethylzinc as an aryl source [C. Bolm, N. Hermanns, M. Kesselgruber, J. P. Hildebrand, *J. Organomet. Chem.* 2001, 624, 157; C. Bolm, N. Hermanns, A. Classen, K. Muñiz, *Bioorg. Med. Chem. Lett.* 2002, 12, 1795]. Enantiomerically enriched diarylmethanols with excellent enantiomeric excess (up to 99% ee) were thus obtained in a straightforward manner. Subsequently, the applicability of air-stable arylboronic acids as an aryl source was also demonstrated [C. Bolm, J. Rudolph, *J. Am. Chem. Soc.* 2002, 124, 14850]. However, these systems require a high catalyst loading (commonly ~10% mol.) to achieve such high enantioselectivity. With the aim of reducing this problem, the use of triphenylborane was recently proposed as an alternative phenyl source in a reaction where the ferrocene-based catalyst is also used (J. Rudolph, F. Schmidt, C. Bolm, *Adv. Synth. Catal.* 2004, 346, 867). It has been applied with difficulties to heteroaromatic aldehydes, for example to 2-thiophenecarbaldehyde.

However, there are still some difficulties to obtain chiral alcohols with a high yield and enantioselectivity without a high amount of catalyst. For their large-scale preparation, the application of highly efficient catalytic systems and enantioselective methods employing inexpensive starting materials and simple purification steps would be most desirable.

On the other hand, the application of these processes to heteroaryl systems is challenging. There is at the present time no example of an enantioselective addition of thienyl- or phenylzinc reagents to heteroaryl aldehydes which comprise one or two nitrogen atoms, such as methyl-pyrazol aldehyde. This is understandable, since substrates containing a nitrogen heteroatom can be expected to form catalytically active complexes (or product complexes) which would usually drastically diminish the selectivity by favoring competing catalytic pathways. Indeed, it is well known in zinc chemistry that various functional groups like esters or nitriles are tolerated on the aldehyde substrates. However, Lewis basic or coordinating functional groups often lead to drastic decreases in enantioselectivity in arylzinc addition reaction, due to their ability to complex to the zinc reagent or the active catalyst. An extreme example of this behavior would be the asymmetric autocatalysis in the addition of zinc reagents to aldehydes as examined by Soai et al. (T. Shibata, H. Morioka, T. Hayase, K. Choji, K. Soai *J. Am. Chem. Soc.* 1996, 471).

Thus, to attain satisfactory ee values by an enantioselective addition reaction, an appropriate coordination of the catalyst system and the aldehyde is required. The results with unusual substrates cannot be predicted, and each addition has to be investigated separately with regard to the substrate.

SUMMARY OF THE INVENTION

We have now surprisingly found that pyrazolcarbaldehydes can be successfully used as substrates for a thienyl transfer reaction. Indeed, the reaction works remarkably well even in the presence of two N on the heteroaromatic part of the aldehyde, providing the desired diheteroaryl-methanols with high conversion and high enantiomeric purity. We have therefore applied this process to the synthesis of the enantiomerically pure intermediates (+)-II and (−)-II and to a process to obtain 2[thienyl(1-methyl-1H-pyrazol-5-yl)methoxy]-N,N-dimethylethanamine and more generally thienylazolylalcoxyethanamines and their enantiomers. This process is contemplated to operate particularly well on an industrial scale and to be satisfactory as regards enantiomeric excess, reduced quantity of catalyst and raw material costs generally. Further, heavy metals are not used, thereby avoiding the presence of potentially toxic impurities. Another advantage is that impurities are easily eliminated.

In one aspect, the present invention relates to a process for the asymmetric addition to a pyrazolcarbaldehyde with a thienyl zinc reagent in the presence of a chiral ligand. Such process allows the preparation of known intermediates of formula (II), which thereafter can yield, by O-alkylation, the desired enantiomers of pharmaceutically active thienylazolylalcoxyethanamines, such as the pharmaceutically active compound 2-[thienyl(1-methyl-1H-pyrazol-5-yl)methoxy]-N,N-dimethylethanamine.

The invention in a further aspect is directed to a process for the preparation of an enantiomerically enriched compound of formula (II):

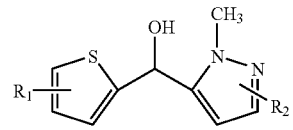

wherein:

$R_1$ and $R_2$ are independently selected from hydrogen, halogen, lower alkyl or aryl;

In which the process includes an enantioselective addition reaction to a methylpyrazolcarbaldehyde compound of formula (IV):

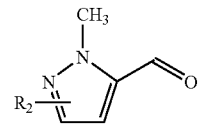

with a thienyl zinc reagent optionally susbtituted on the thienyl ring, in the presence of a chiral ligand.

In one preferred embodiment, $R_1$ is H.

In another preferred embodiment, $R_2$ is H.

Other aspects, features and advantages of the invention will be more fully apparent from the ensuing disclosure and appended claims.

DETAILED DESCRIPTION OF THE INVENTION

In one aspect, the present invention relates to a process for the preparation of an enantiomerically enriched compound of formula (II):

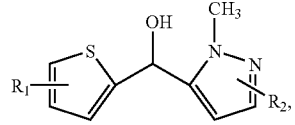

wherein:

$R_1$ and $R_2$ are independently selected from hydrogen, halogen, lower alkyl and aryl; In which the process includes an enantioselective addition reaction to a methyl pyrazolcarbaldehyde compound of formula (IV):

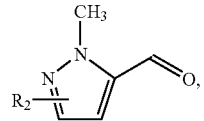

with a thienyl zinc reagent optionally substituted on the thienyl ring, in the presence of a chiral ligand.

It will be readily apparent to the person skilled in the art that the process is also applicable for the thienyl addition to other aldehydes having a different nitrogen-containing heterocycle instead of the methylpyrazole ring, such as methylpyrrole, methyl imidazole or methyl triazole.

The term "lower alkyl" as used herein refers to a linear or branched hydrocarbon chain that contains 1 to 4 carbon atoms, such as methyl, ethyl, propyl, isopropyl, butyl, isobutyl, sec-butyl or tert-butyl.

By "thienyl zinc reagent optionally substituted on the thienyl ring", we refer to a thienyl zinc reagent which can be substituted at the 2, 3, 4 or 5 position of the thienyl ring by a halogen, a lower alkyl or an aryl group.

Such process gives the desired products of formula II with a high conversion and enantiomeric excess. This process has the further advantage that the zinc salts used or formed during the reaction are easily removed by aqueous work-up. The product of formula II is especially useful in the preparation of the enantiomers of the above mentioned thienylazolylalcoxyethanamines. Different compounds can be obtained depending on the substituents present on the thienyl or N-containing heterocyclic rings.

We discuss below the different reagents and conditions for the process of the invention.

Pyrazolcarbaldehyde (Azolylcarbaldehyde)

The synthesis of methylpyrazolcarbaldehyde (IV), which is the essential starting material for the addition route, is known to the person skilled in the art. For example, (IV) can be easily prepared through the lithiation of 1-methylpyrazole (V):

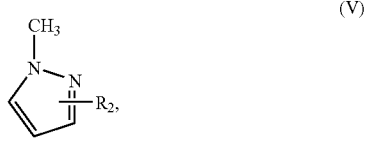
(V)

and concomitant quenching with dimethyl formamide (DMF). The reaction product then is hydrolyzed, for example with water or sodium acetate buffer (pH 4.5), and either employed directly or after distillation (scheme I). Residual amounts of DMF do not appear to influence the selectivity of the subsequent addition process.

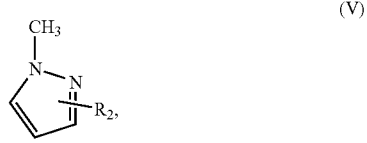
(V)

Optimal conditions for the lithiation are found in the literature (T. E. Smith, M. S. Mourad, A. J. Velander, *Heterocycles* 2002, 57, 1211) and can be employed for the formylation reaction of the appropriate substrate. If necessary diethyl amine can be used to prevent the deprotonation of the N-methyl group, and normally 10 mol % is sufficient. Preferably, THF is used as the solvent, and in this case no additive is necessary. The deprotonation reaction preferably is performed below −10° C. (usually at −20° C.) to prevent the formation of side products by ring-opening of THF. To purify the obtained 1-methylpyrazolcarbaldehyde, distillation or extractive workup with an organic solvent can be used to remove the by-products. Otherwise, as previously mentioned, the aldehyde can be used directly for the addition.

A person skilled in the art would readily know how to prepare other aldehydes having different nitrogenated heterocycles, such as pyrrole, imidazole and triazole, or different patterns of substitution.

Thienyl Zinc Reagent

The thienylzinc reagent can be prepared in situ by a transmetallation reaction of a thienylboron reagent with dimethyl- or diethyl-zinc. The active species are presumably a mixed thienyl-ethyl-zinc or thienyl-methyl-zinc.

Among the suitable thienyl-boron reagents, thienylboronic acid, trithienylborane or 2-aminoethyl dithienylborinate, depicted below:

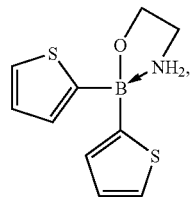

is preferably selected. More preferably, the thienyl-boron reagent is 2-aminoethyl dithienylborinate. Stable complexes of thienyl boranes are also preferred. The thienyl zinc can optionally have an $R_1$ substituent as defined above.

Chiral Ligand

With the aim of enantioselectively synthesizing a compound of formula (II) by an enantioselective addition reaction, the addition reaction must be carried out in the presence of a chiral catalyst or ligand, which forms the active catalyst in situ by reaction with the zinc reagent. That means that the ligand (or catalyst) must have at least one element of chirality, e.g., one or more stereocenters or elements of planar chirality.

In principle, there is a great variety of N,O—, N,N—, N,S—, N,Se— or O,O-ligands that can be used in the process of the invention, and all of them have to be in enantiomerically pure form. There are in the art about 600 known ligands for this type of reaction. Most of them can be found, for example, in a recent review on catalytic asymmetric organozinc additions to carbonyl compounds [L. Pu, H.-B. Yu, Chem. Rev. 2001, 101, 757]. The nomenclature N,O—, N,N—, N,S—, N,Se— or O,O— refers to ligands that have at least these two coordinating heteroatoms.

In a preferred embodiment of the present invention, N,O-ligands are employed. In general, they are derived from β-amino alcohols and therefore have two carbon atoms between the heteroatoms. However, some of the ligands that can be usefully employed in this reaction are those which present three carbon atoms between the heteroatoms.

These ligands react with the zinc reagent forming a zinc-alcoxide complex which is more Lewis-acidic than the other present zinc species (reagent and product). Additionally, it is a Lewis-base catalyst (usually at the oxygen atom). This zinc-alcoxide complex formed in situ is the active catalyst.

More preferably, the O is an alcohol. In this case, the preferred ligands have a structure-type (V) such as described below:

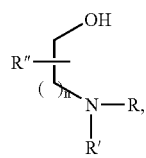
(V)
wherein n is 0 or 1.
Typical ligands useful in this addition reaction include the following compounds, their enantiomers, and derivatives thereof:
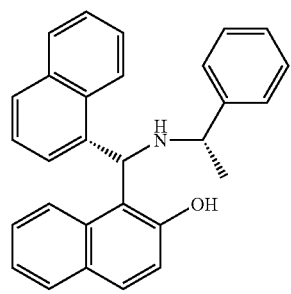
(S,S)-499
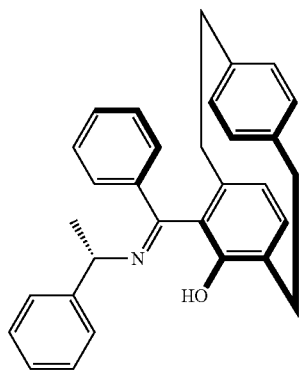
S$_p$,S-TD10a
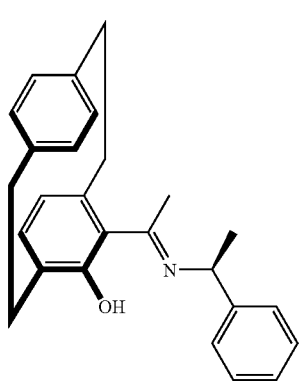
(R$_p$,S)-311a
-continued
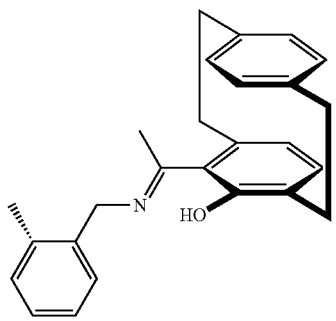
SD-311b
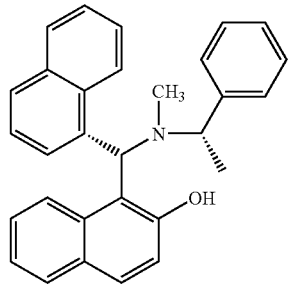
SD-498a
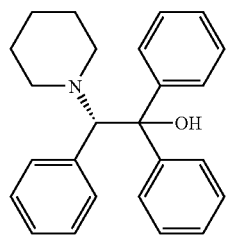
(S)-2-piperidinyl-1,1,2-triphenylethanol
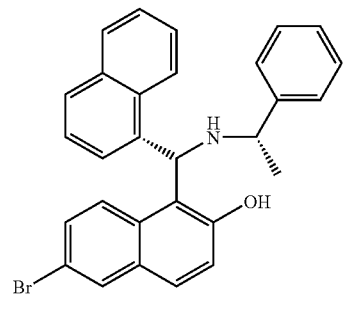
SD522
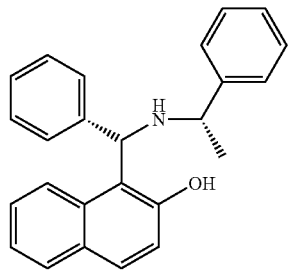
SD504

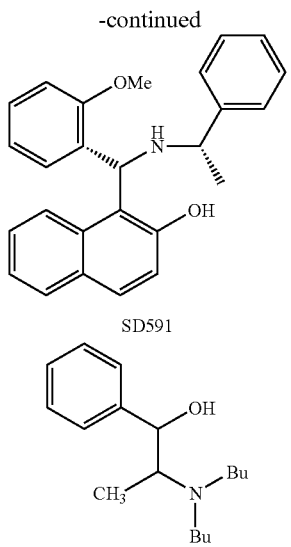

SD591

(1R, 2S)-(-)dibuthylamine-1-phenyl-propanol.

These ligands are available in both enantiomeric forms, allowing the selective synthesis of both enantiomers of the desired alcohol.

By way of example, good results have been obtained with sd311a together with dimethylzinc and with (S)-2-piperidinyl-1,1,2-triphenylethanol (SD-286), which is commercially available, together with diethylzinc.

The reaction that takes place between the zinc reagent and the ligand leads to a complex of formula (VI):

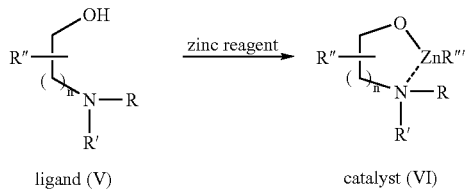

ligand (V)    catalyst (VI)

wherein n is 0 or 1 and R''' is thienyl, ethyl or methyl.

This zinc alkoxide complex (VI) is the active catalyst in the addition reaction, which subsequently coordinates with the pyrazolcarbaldehyde in such a way as to induce the enantioselective addition of the phenyl group to the aldehyde.

The concentration of the ligand should be low to reduce costs, but sufficient to provide good ee. The ligands are preferably used in amounts of 0.1 to 100 mol %, more preferably 1 to 20 mol %, and most preferably 5 to 10 mol %. The use of more than the optimal amount of ligand is uneconomical, and in some cases can lead to a lower selectivity. On the contrary, using less than the optimal amount of ligand diminishes the selectivity, due to a stronger influence of the non-catalysed and non-enantioselective background reaction.

Solvent

Suitable solvents for the process of the invention are known from similar reactions and can be found in the above-mentioned references. Preferred solvents include non-coordinating hydrocarbons such as pentane, hexane, heptane; aromatic solvents such as benzene, toluene; chlorinated solvents such as dichloromethane and 1,2-dichloroethane; and weakly coordinating solvents such as diethyl ether and methyl-tert-butyl ether (MTBE). The most preferred solvents are toluene and hexane. These solvents allow the optional O-alkylation to be carried out in the same reaction mixture.

To perform the process, a mixture of ligand and the compounds that form the zinc reagent can be prepared and stirred before the addition of the aldehyde. Usually, a pre-stirring is presumed to be beneficial for the selectivity, because the deprotonation of the ligand by the zinc reagent to yield the active catalyst requires a certain amount of time.

Unexpectedly, it has been found that higher enantiomeric excess is achieved if short pre-stirring times are used. The highest selectivities were obtained upon simultaneous addition of aldehyde and dialkylzinc. Thus, in a preferred embodiment these reagents are simultaneously added. Once the aldehyde is added to the mixture of ligand and zinc reagent, the reaction time ranges between 1 hour and 24 hours.

The concentration of the aldehyde in the reaction is preferably low, e.g., in a range of from 0.01 molar to 2 molar, more preferably in a range of from 0.1 to 1 molar, and most preferably at a concentration of about 0.1 molar. Although in some cases it has been seen that enantioselectivity increases at less concentrations, this is not suitable for an industrial process. In these cases a proper balance between enantioselectivity and adequate concentrations has to be found.

The process of the invention can be carried out at temperature in a range of from -40 to 100° C. Preferably, temperatures between -20 and 20° C. are used. Most preferably, the reactions are carried out at temperature in the vicinity of about -10° C. The person skilled in the art can readily determine without undue experimentation the optimal temperature for each combination of reagents. The enantioselectivity of the reaction can also be dependent on the reaction temperature.

The process of the invention can also comprise the presence of additives, for example to improve the enantioselectivity by scavenging or complexing Lewis-acidic zinc salts present in the reaction or formed as products.

Suitable additives are for example alcohols, amines or derivatives of polyethyleneglycol. More preferably the additive is selected from polyethyleneglycols such as DiMPEG 1000, DiMPEG 2000, PEG 750, PEG 1000, PEG 2000, monoMPEG 2000 and PE-block-PEG, or from compounds such as 1,4-dioxane, i-propanol and triethylamine.

In one preferred embodiment, the process is directed to the synthesis of each of the following alcohols of formula II with the highest possible enantiomeric purity:

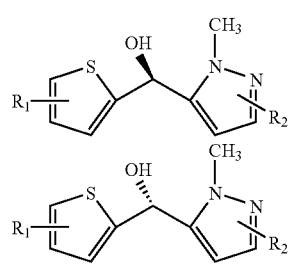

wherein $R_1$ and $R_2$ are as defined above.

It will be readily apparent to the person skilled in the art that the process of the invention is also applicable for the thienyl addition to other aldehydes having a different nitrogen-containing heterocycle instead of the pyrazole ring, such as pyrrole, imidazole or triazole.

The obtained alcohol can be purified through chromatography or crystallization; the zinc salts used are easily removed by aqueous work-up.

Alternatively, the alcohol can advantageously be used without further purification in the next step, which can be carried out in the same reaction medium.

Thus, in another aspect, the invention relates to a process as defined above which further comprises the step of O-alkylation of an enantiomerically enriched compound of formula (II) to yield the desired enantiomer of a pharmaceutically active compound, as described in International Patent Publication WO 99/52525. To this end the compound of formula (II) is treated with an amine of formula

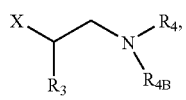

wherein

X is a suitable leaving group such as halogen, more preferably chlorine, bromine or iodine; a reactive esterified hydroxyl, for example arylsulfonyloxy such as phenylsulfonyloxy; tosyloxy; mesyloxy; $C_{1-4}$ alkyl sulfonyloxy, for example methanesulfonyloxy; arylphosphoryloxy, for example diphenylphosphoryloxy, dibenzylphosphoryloxy or a $C_{1-4}$ alkyl phosphoryloxy, for example dimethylphosphoryloxy, and $R_3$, $R_4$ and $R_{4B}$ are independently selected from H and lower alkyl.

Preferably, $R_3$ is hydrogen.

Preferably, $R_4$ and $R_{4B}$ are independently selected from H and methyl.

In one embodiment, both $R_4$ and $R_{4B}$ are methyl.

A particularly preferred amine for the step of O-alkylation is X—$CH_2$—$CH_2N(Me)_2$. More preferably, X is chlorine.

The O-alkylation has been described in International Patent Publication WO 99/52525, the disclosure of which hereby is incorporated herein in its entirety.

The alkylation preferably is carried out directly in the same reaction medium resulting from the process of the invention, without further purification of the carbinol. In general, the O-alkylation is carried out in conditions of phase transfer, using for example 2-chloro-N,N,-dimethylethylamine (other leaving groups instead of chloro are possible), an alkaline aqueous solution such as NaOH or KOH, in the presence of a catalyst such as a quaternary ammonium salt. Accordingly, the same solvent as the one used in the process of the invention is used, such as toluene. In these conditions we have the further advantage that impurities such as any remaining zinc salts are also eliminated through the aqueous phase.

The resulting product of formula I is enantiomerically enriched, and it can be further purified using polar organic solvents. Further, a pharmaceutically acceptable salt of the obtained compound can be formed. For example, the citrate salt can be prepared by dissolving the amine of formula I in ethanol and treating the solution with citric acid monohydrate. The preparation of other salts will be readily apparent to the person skilled in the art.

The following examples will further illustrate the invention, and are not to be interpreted as limiting, as regards the scope of the invention.

EXAMPLES

Example 1

Synthesis of 2-methyl-2H-pyrazole-3-carbaldehyde

In a dry 50 ml vial is placed a solution of 1.642 g (20 mmol) N-methylpyrazole in 30 ml dry THF. The mixture is cooled to −20° C. and while stirring 8 ml (20 mmol, 2.5M in hexane) n-BuLi-solution is slowly added. The reaction mixture is stirred for 2.5 hours at −20° C. With vigorous stirring 4.7 ml (4.39 g, 60 mmol) dry DMF is slowly added at −20° C. and the mixture is kept at this temperature for 1 hour. The reaction mixture then is poured into 100 ml of a 1 M acetic acid/sodium acetate buffer (pH 4.5), 50 ml MTBE is added and the organic layer is separated, washed with 50 ml saturated $Na_2CO_3$-solution to remove excess acetic acid (extraction with ethyl acetate leads to DMF in the final product). The organic layer is separated, dried with $MgSO_4$ and the solvent is removed using a rotary evaporator. The crude product is purified by vacuum distillation (bp: 67° C., 21 mbar). Three preparations which were distilled together yielded 5.969 g (54 mmol, 90%) of the title compound.

$^1$H—NMR (300 MHz, $CDCl_3$): 4.18 (s, 3H, $CH_3$—N), 6.91 (d, 1H, $^3J$=2.0 Hz, CH═C—N), 7.53 (d, 1H, $^3J$=2.0 Hz, CH═N), 9.87 (s, 1H, CH═O) ppm.

$^{13}$C—NMR (100 MHz, $CDCl_3$): 39.31 ($CH_3$—N), 114.78 (CH═C—N), 138.54 (CH═N), 138.98 (CH═C—N), 179.83 (CH═O) ppm.

Example 2

Synthesis of (2-methyl-2H-pyrazole-3-yl)-thiophene-2-yl-methanol

A) With ligand SD311a and dimethylzinc at 10° C.

50 mg (0.21 mmol) 2-aminoethyl-dithienyl-borinate and 3.7 mg (0.010 mmol) of ligand SD311a (4 mol %) are placed in a 20 ml vial. The vial is closed and flushed with argon. Dry toluene (2 mL) is added and the vial is placed in a cooling bath of 10° C. Dimethylzinc (0.35 mL, 0.7 mmol, 2M solution in toluene) and 25 μl (0.25 mmol) 2-methyl-2H-pyrazole-3-carbaldehyde is added and the reaction mixture is stirred for at least 12 hours at 10° C. The reaction is quenched by addition of 2 mL of 1 M HCl with vigorous stirring. The reaction mixture is placed in a separation funnel, and 10 ml 1 M HCl and approx. 25 ml MTBE are added. The organic layer is washed with 15 ml of saturated $Na_2CO_3$-solution, dried with $MgSO_4$ and the solvent is removed by a rotary evaporator. The product is further purified by chromatography on silica to yield the title compound (25 mg, 52%) in 67% ee.

Evaluation of enantiomeric excess:

HPLC Column: Diacel Chiralpak AD 250×4 mm heptane/propane-2-ol 93/7

Flow: 0.5 ml/min; Temp.: 15° C.; det.: 230 nm

Ret-Times: 32.5 min/34.5 min $^1$H—NMR (400 MHz, $CDCl_3$): 3.64 (s, 3H, $CH_3$—N), 5.73 (s, 1H, OH), 6.03 (s, 1H, CH-OH), 6.13 (d, 1H, $^3J$=1.92 Hz, CH—CH═C—N), 6.82 (dt, 1H, $^3J$=3.57, $^4J$=1.10 Hz, CH═C—S—CH), 6.92 (dd, 1H, $^3J$=4.94, $^3J$=3.57 Hz, CH=CH—S—C), 7.19 (d, 1H, ³J=1.92 Hz, CH—CH=C—N), 7.24 (dd, 1H, ³J=4.94, ⁴J=1.10 Hz, S—CH=CH) ppm.

¹³C-NMR (100 MHz, CDCl₃): 36.78 (CH₃—N), 64.15 (CH—OH), 105.15 (CH=C—N), 124.62 (CH=C—S), 125.28 (CH=CH—S), 126.53 (CH=CH—S), 137.41 (CH—CH=N), 143.94 (CH=C—S), 145.16 (CH=C—N) ppm.

B) With ligand (S)-2-piperidinyl-1,1,2-triphenylethanol and diethylzinc at −10° C.

50 mg (0.21 mmol) 2-aminoethyl-dithienyl-borinate and 9.3 mg (0.025 mmol) of ligand (S)-2-piperidinyl-1,1,2-triphenylethanol (10 mol %) are placed in a 20 ml vial. The vial is closed and flushed with argon. Dry toluene (2 mL) is added and the vial is placed in a cooling bath of −10° C. Diethylzinc (0.7 mL, 0.7 mmol, 2M solution in toluene) and 25 μl (0.25 mmol) 2-methyl-2H-pyrazole-3-carbaldehyde are added and the reaction mixture is stirred for at least 12 hours at −10° C. Work-up is conducted as described in Example 2ᵃ to yield the title compound (24 mg, 51%) in 70% ee.

What is claimed is:

1. A process for the preparation of an enantiomerically enriched compound of formula (II):

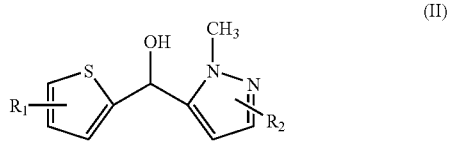

(II)

wherein:
R₁ and R₂ are independently selected from hydrogen, halogen, lower alkyl and aryl; which comprises an enantioselective addition reaction to a methylpyrazolcarbaldehyde compound of formula (IV):

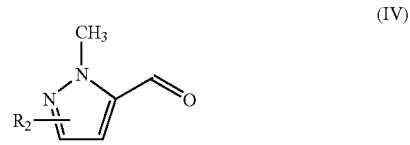

(IV)

with a thienyl zinc reagent optionally substituted on the thienyl ring, in the presence of a chiral ligand.

2. A process according to claim 1, wherein the methylpyrazolcarbaldehyde is replaced by a methyl pyrrolecarbaldehyde, a methyl imidazolecarbaldehyde or a methyl triazolecarbaldehyde.

3. A process according to claim 1, wherein the thienyl zinc reagent is prepared in situ by a transmetallation reaction of a thienylboron reagent with dimethyl-zinc or diethyl-zinc.

4. A process according to claim 3, wherein the thienylboron reagent is selected from the group consisting of: thienylboronic acid; trithienylborane; and 2-aminoethyl dithienylborinate,

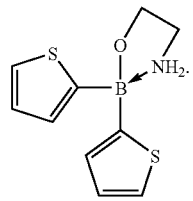

5. A process according to claim 1, wherein the chiral ligand is a N,O—, N,N—, N,S—, N,Se— or O,O-ligand in its enantiomerically pure form.

6. A process according to claim 1, wherein the chiral ligand is a N,O-ligand.

7. A process according to claim 6, wherein the O is an alcohol.

8. A process according to claim 6, wherein the N,O-ligand comprises a ligand selected from the group consisting of the following compounds:

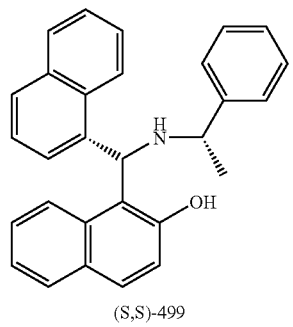

(S,S)-499

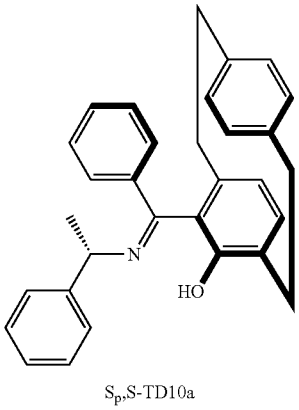

Sp,S-TD10a

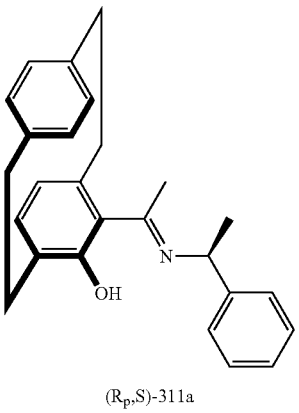

(Rp,S)-311a

-continued

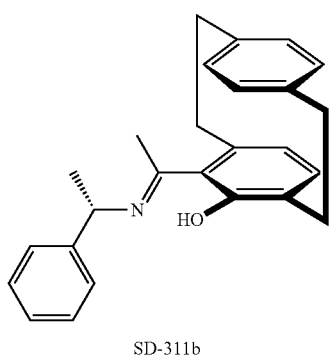

SD-311b

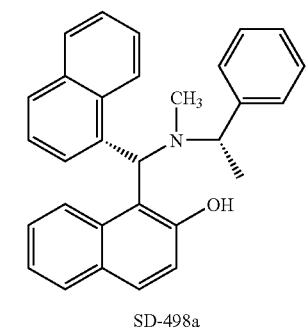

SD-498a

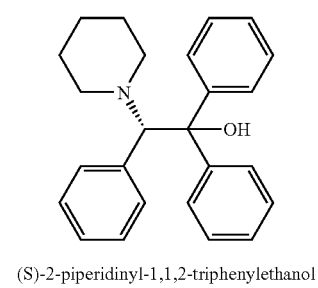

(S)-2-piperidinyl-1,1,2-triphenylethanol

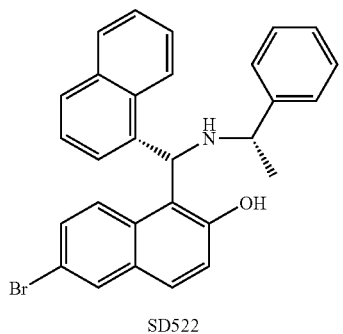

SD522

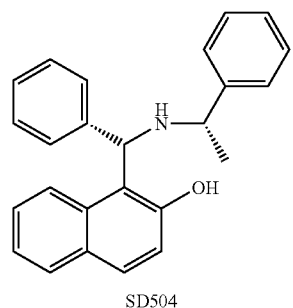

SD504

-continued

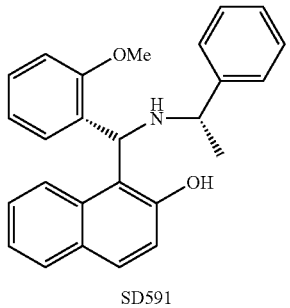

SD591

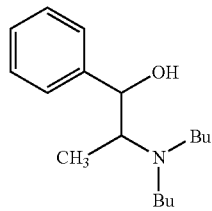

(1R, 2S)-(-)dibuthylamine-1-phenyl-propanol.

9. A process according to claim 1, wherein the ligand is used in an amount in a range of from 1 to 20 mol %.

10. A process according to claim 1, wherein the ligand is used in an amount in a range of from 5 to 10 mol %.

11. A process according to claim 1, wherein the enantioselective addition reaction is conducted at temperature in a range of from −20° C. to 20° C.

12. A process according to claim 1, wherein the carbaldehyde is at a concentration in a range of from 0.01 molar to 2 molar.

13. A process according to claim 1, wherein the enantioselective addition reaction is conducted in solvent medium.

14. A process according to claim 13, wherein the solvent medium comprises toluene or hexane.

15. A process according to claim 1, which further comprises an O-alkylation of the enantiomerically enriched compound of formula II, with an amine of the formula

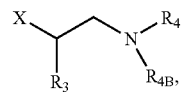

wherein X is a leaving group selected from halogen and reactive esterified hydroxyl, and $R_3$, $R_4$ and $R_{4B}$ are each independently selected from H and lower alkyl.

16. A process according to claim 15, wherein the O-alkylation is carried out, without an intermediate separation or purification step.

17. A process for the preparation of a precursor alcohol of (±)-2-[thienyl(1-methyl-1H-pyrazol-5-yl)methoxy]-N,N-dimethyletanamine, comprising asymmetric addition of a metalated thienyl reagent to a pyrazolcarbaldehyde in the presence of a chiral ligand to yield said precursor alcohol.

18. The process of claim 17, further comprising O-alkylating said chiral alcohols to yield corresponding pharmaceutically active thienylazolylalcoxyethanamines.

19. A process for preparation of thienylazolylalcoxyethanamine, comprising asymmetric addition of a metalated thienyl reagent to a pyrazolcarbaldehyde in the presence of a chiral ligand to yield chiral alcohol, and O-alkylating said chiral alcohol to yield said thienylazolylalcoxyethanamine.

20. A process according to claim 19, wherein the O-alkylation is carried out without an intermediate separation or purification step.

* * * * *

UNITED STATES PATENT AND TRADEMARK OFFICE
CERTIFICATE OF CORRECTION

PATENT NO.        : 7,078,531 B1
APPLICATION NO.   : 11/041638
DATED             : July 18, 2006
INVENTOR(S)       : Antoni Torrens Jover et al.

It is certified that error appears in the above-identified patent and that said Letters Patent is hereby corrected as shown below:

In the References Cited: Other Publications section, page 1, second column, "Rudolph, Jens, et al., *High Entantioselective Synthesis of Secondary Alcohols Using Triphenylborane, Adv. Synth. Catal.* Vol. 346, (2004) 867-872" should be -- Rudolph, Jens, et al., *Highly Entantioselective Synthesis of Secondary Alcohols Using Triphenylborane, Adv. Synth. Catal.* Vol. 346, (2004) 867-872 --

Column 5, lines 4-5, "methylpyrazole ring, such as methylpyrrole" should be -- methyl pyrazole ring, such as methyl pyrrole --.

Column 5, line 30, "1-methylpyrazole" should be -- 1-methyl pyrazole --.

Column 5, lines 47-55, " 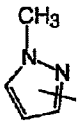 " should be

--  (Scheme I) --

Signed and Sealed this

Fifth Day of December, 2006

JON W. DUDAS
*Director of the United States Patent and Trademark Office*